(12) United States Patent
Hellberg et al.

(10) Patent No.: US 6,211,226 B1
(45) Date of Patent: Apr. 3, 2001

(54) 11-AZA PROSTAGLANDINS FOR THE TREATMENT OF GLAUCOMA AND OCULAR HYPERTENSION

(75) Inventors: Mark R. Hellberg, Arlington; Peter G. Klimko, Fort Worth, both of TX (US)

(73) Assignee: Alcon Laboratories, Inc., Fort Worth, TX (US)

(*) Notice: Subject to any disclaimer, the term of this patent is extended or adjusted under 35 U.S.C. 154(b) by 0 days.

(21) Appl. No.: 09/430,533

(22) Filed: Oct. 29, 1999

Related U.S. Application Data

(60) Provisional application No. 60/112,658, filed on Dec. 17, 1998.

(51) Int. Cl.[7] .................. A61K 31/40; C07D 207/12; C07D 207/08; C07D 207/04
(52) U.S. Cl. ................. 514/424; 514/428; 548/556; 548/568; 548/572
(58) Field of Search ................. 548/556, 568, 548/572; 514/424, 428

(56) References Cited

U.S. PATENT DOCUMENTS

| | | | |
|---|---|---|---|
| 4,003,911 | * | 1/1977 | Scribner et al. ............... 548/556 |
| 4,299,970 | * | 11/1981 | Cassidy et al. ............... 560/39 |
| 4,599,353 | | 7/1986 | Bito . |
| 4,952,581 | | 8/1990 | Bito et al. . |
| 5,093,329 | | 3/1992 | Woodward . |
| 5,321,128 | | 6/1994 | Stjernschantz et al. . |
| 5,420,298 | * | 5/1995 | Edwards et al. ............... 548/556 |
| 5,773,471 | | 6/1998 | Oguchi et al. . |
| 5,811,443 | | 9/1998 | DeSantis et al. . |

FOREIGN PATENT DOCUMENTS

| | | |
|---|---|---|
| 4229050 A1 | 3/1994 | (DE) . |
| 0330 511 A2 | 8/1989 | (EP) . |
| 0561 073 A1 | 9/1993 | (EP) . |
| WO 92/08465 | 5/1992 | (WO) . |

OTHER PUBLICATIONS

Alm, *The Potential of Prostaglandin Derivatives in Glaucoma Therapy*, Current Opinion in Ophthalmology, 4(11):44–50 (1993).

Giuffre, The Effects of Prostaglandin $F_{2\alpha}$ in the Human Eye, Graefe's Archive Ophthalmology, 222:139–141 (1985).

Holzapfel et al., S. Afr. Tydskr. Chem, 38(2):65–72 (1985).

Kerstetter et al., *Prostaglandin $F_{2\alpha}$–1–Isopropylester Lowers Intraocular Pressure Without Decreasing Aqueous Humor Flow*, American Journal of Ophthalmology, 105:30–34 (1988).

Nakajima et al., *Effects of Prostaglandin $D_2$ and its analogue, BW245C, on Intraocular Pressure in Humans*, Graefe's Arch Clin Exp Ophthalmol 229:411–413 (1991).

Rozing, et al., Heterocycles 7(1):123–9 (1977).

Verdoorn et al, *Stereospecific Synthesis of Intermediates for 11–AZA–11–Deoxy and 11–Azaprostaglandin Analgoues From L-Arabinase*, Synthetic Communications, 22(13):1813–29 (1992).

* cited by examiner

Primary Examiner—Deborah C. Lambkin
(74) Attorney, Agent, or Firm—Barry L. Copeland

(57) ABSTRACT

11-aza analogs of $PGF_{2\alpha}$ and methods of their use in treating glaucoma and ocular hypertension are disclosed.

20 Claims, No Drawings

11-AZA PROSTAGLANDINS FOR THE TREATMENT OF GLAUCOMA AND OCULAR HYPERTENSION

CROSS REFERENCE TO RIELATED APPLICATION:

This application draws priority from U.S. Provisional Application Serial No. 60/112,658 filed Dec. 17, 1998.

BACKGROUND OF THE INVENTION

The present invention relates to novel compounds and methods for the treatment of glaucoma and ocular hypertension. In particular, the present invention relates to the use of certain 11-aza analogs of F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). Of interest in the present invention are compounds which are believed to exhibit IOP lowering mechanisms similar to those exhibited by $PGF_{2\alpha}$ (an F-series prostaglandin):

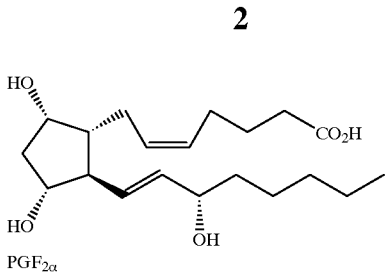

$PGF_{2\alpha}$

The relationship of $PGF_{2\alpha}$ receptor activation and IOP lowering effects is not well understood. It is believed that $PGF_{2\alpha}$ receptor activation leads to increased outflow of aqueous humor. Regardless of the mechanism, $PGF_{2\alpha}$ and certain of its analogs have been shown to lower IOP (Giuffre, The Effects of Prostaglandin $F_{2\alpha}$ the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, a number of these types of molecules have also been associated with undesirable side effects resulting from topical ophthalmic dosing. Such effects include an initial increase in IOP, breakdown of the blood aqueous barrier and conjunctival hyperemia (Alm, The Potential of Prostaglandin Derivatives in Glaucoma Therapy, *Current Opinion in Ophthalmology*, volume 4, No. 11, pages 44–50 (1993)). Based on the foregoing, a need exists for the development of molecules that may activate the $PGF_{2\alpha}$ receptor yielding a more efficacious lowering of IOP, while exhibiting fewer or reduced side effects.

Stjernschantz et al. (U.S. Pat. No. 5,321,128), Woodward et al., (U.S. Pat. No. 5,093,329), Chan et al. (WO 92/08465) and Ueno et al. (EP 330 511 $A_2$) have suggested synthetic prostaglandin analogs to reduce selectively or to eliminate altogether the side effects while maintaining the IOP-lowering effect. These synthetic prostaglandins, like their natural counterparts, all possess the core cyclopentane ring suggesting that it is important for IOP lowering activity.

An agent which exhibits comparable or improved efficacy, but with reduced side effects when compared to other agents, is said to have an improved therapeutic profile. It is an object of this invention to provide a class of IOP lowering agents with an improved therapeutic profile over $PGF_{2\alpha}$ and methods of their use. It has now unexpectedly been discovered that the presently claimed 11-aza analogs of $PGF_{2\alpha}$, in which the cyclopentane ring of endogenous prostaglandins is replaced by a pyrrolidine ring, meet this objective. Certain 11-aza analogs of prostaglandins have been reported in the literature (see, e.g., Rozing et al., *Heterocycles*, 7:123–9 (1977); Verdoorn et al., *Synthetic Communications*, 22:1813–29 (1992); and Holzapfel et al., *South African Journal of Chemistry*, 38:65–72 (1985), which are incorporated herein by reference). The compounds and methods of the present invention, however, are neither disclosed nor suggested in the foregoing art.

SUMMARY OF THE INVENTION

The present invention is directed to novel compounds and compositions, and methods of their use in treating glaucoma and ocular hypertension. In particular, the present invention provides certain classes of pyrrolidine analogs of the naturally occurring cyclopentane ring-containing prostaglandins, and methods of their use in treating glaucoma and ocular hypertension.

DETAILED DESCRIPTION OF THE INVENTION

It has unexpectedly been found that 11-aza prostaglandin analogs of the present invention exhibit an improved therapeutic profile in the treatment of glaucoma and ocular hypertension when compared to natural (cyclopentane) prostaglandins and many of their known analogs. The 11-aza prostaglandin analogs of the present invention may also be used to treat optic nerve disorder by retarding visual field loss or improving visual acuity in the manner described in U.S. Pat. No. 5,773,471, the disclosure of which is incorporated herein by this reference.

It is further contemplated that the compounds of the present inventions can be used with other medicaments known to be useful in the treatment of glaucoma or ocular hypertension, either separately or in combination. For example, the 11-aza prostaglandin analogs of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443); and (iv) cholinergic agonists, such as pilocarpine. The disclosures of U.S. Pat. Nos. 4,952,581 and 5,811,443 are incorporated herein by this reference.

The 11-aza prostaglandin analogs of the present invention have the following formula I:

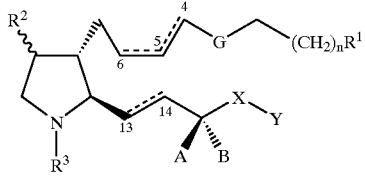

I wherein:
$R^1 = CO_2R$, $CONR^4R^5$, $CH_2OR^6$, or $CH_2NR^7R^8$; where:
  R=H or cationic salt moiety, or $CO_2R$ forms a pharmaceutically acceptable ester moiety;
  $R^4$, $R^5$=same or different=H or alkyl;
  $R^6$=H, acyl, or alkyl;
  $R^7$, $R^8$=same or different=H, acyl, or alkyl; with the proviso that if one of
  $R^7$, $R^8$=acyl, then the other=H or alkyl;
n=0 or 2;
G=$CH_2$ or O;
$R^2$=H, OH, acyloxy, or alkoxy;
- - - =single or non-cumulated double bond, with the provisos that when G=O, a single bond exists between carbons 4 and 5, and that if a double bond is present between carbons 13 and 14 that it be of the trans configuration;
$R^3$=H,$R^{11}$, $COR^{11}$, or $CO_2R^{11}$, where $R^{11}$=alkyl;
one of A, B=H, the other=F, OH, acyloxy, or alkoxy;
or A-B=$O(CH_2)_2O$ or O as a carbonyl;
X=$(CH_2)_q$ or $(CH_2)_qO$; where q=1–6; and Y=a phenyl ring optionally substituted with alkyl, halo, trihalomethyl, alkoxy, acyl, acyloxy, amino, alkylamino, acylamino, or hydroxy; or
X-Y=$(CH_2)_pY^1$; where p=0–6; and $Y^1 =$ 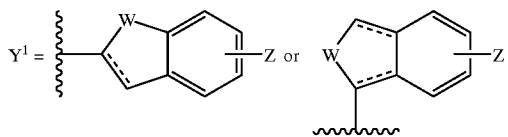

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy; and
- - - =single or double bond.

Included within the scope of the present invention are the individual enantiomers of the title compounds, as well as their racemic and non-racemic mixtures. The individual enantiomers can be produced by any one of a number of methods, e.g., by purification of a racemic sample by chiral HPLC (*A Practical Guide to Chiral Separations* by HPLC, G. Subramanian, Ed., VCH Publishers: New York, 1994; *Chiral Separations* by HPLC, A. M. Krstulovic, Ed., Ellis Horwood Ltd. Publishers, 1989), or by enantioselective hydrolysis of a racemic carboxylic acid ester by an enzyme (Ohno, M.; Otsuka, M. *Organic Reactions*, volume 37, page 1 (1989)). Also included within the scope of the present invention are the individual isomers of the disclosed compounds substantially free of their respective enantiomers.

As used herein, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic may be either alpha (α) or beta (β). The carbon numbering is as indicated in formula application, i.e. non-toxic and non-irritating. Wavy line attachments indicate that the configuration I, even when n=2. Dashed lines on bonds [e.g., between carbons 4 (C-4) and 5 (C-5] indicate a single or double bond. Two solid lines present specify the configuration of the relevant double bond. Hatched lines indicate the α configuration. A solid triangular line indicates the β configuration.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred compounds of the present invention are those of formula I above, wherein:

$R^1$=$CO_2R$, where R=H or $CO_2R$ forms an ophthalmically acceptable ester moiety;

n=0;

G=$CH_2$;

- - - =a single or non-cumulated double bond, with the provisos that a double bond between carbons 4 and 5 may not be of the trans configuration, and that a trans double bond exists between carbons 13 and 14;

$R^2$=OH in the alpha configuration;

$R^3$=H;

A=H, and B=OH;

X=$CH_2CH_2$ or $CH_2O$;

Y=phenyl optionally substituted with halo or trihalomethyl;

or, X-Y=$(CH_2)_p Y^1$, where p=0 and $Y^1 =$ 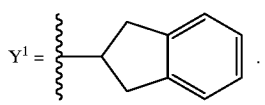 .

Most preferred of the foregoing compounds are those having an ophthalmically acceptable ester moiety of the formula $CO_2R$, wherein R is alkyl, preferably C2–C4 alkyl, and especially isopropyl. Examples of such most preferred compounds are the following:

| Compound Number | Compound Name | Compound Structure |
|---|---|---|
| II | (5Z,13E)-(9R,15R)-11-Aza-9,15-dihydroxy-16-(3-trifluromethyl)phenoxy-17,18,19,20-tetranor-5,13-prostadienoic acid isopropyl ester | 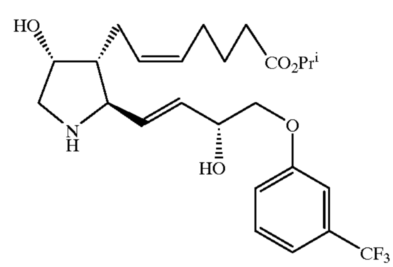 |
| III | (5Z,13E)-(9R,15S)-11-Aza-9,15-dihydroxy-15-(2-indanyl)-16,17,18,19,20-pentanor-5,13-prostadienoic acid isopropyl ester | 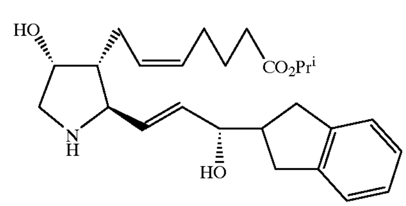 |

-continued
| Compound Number | Compound Name | Compound Structure |
| --- | --- | --- |
| IV | (4Z,13E)-(9R,15R)-11-Aza-16-(3-chlorophenoxy)-9,15-dihydroxy-17,18,19-20-tetranor-4,13-prostadienoic acid isopropyl ester | 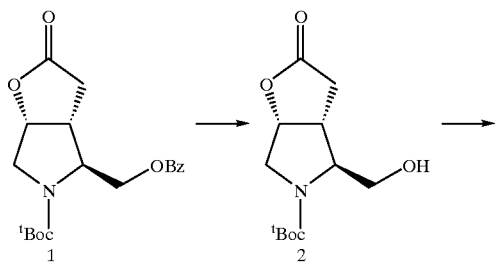 |
EXAMPLE 1:
Synthesis of II
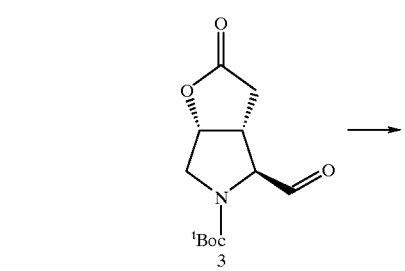
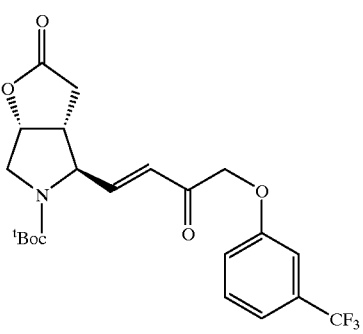
-continued
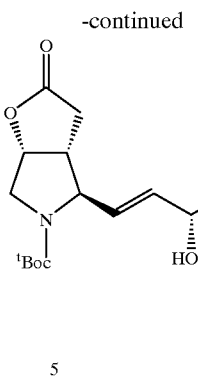
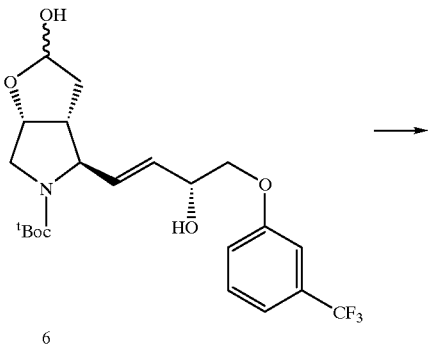
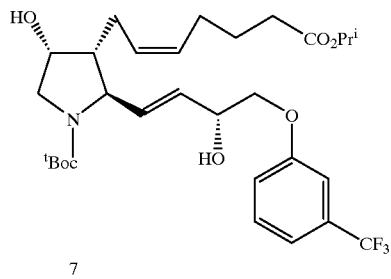

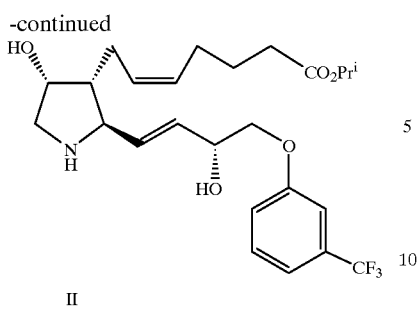

II

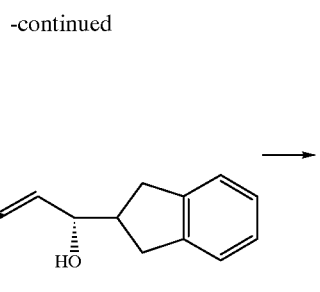

(5Z,13E)-(9R,15R)-11-Aza-9,15-dihydroxy-16-(3-trifluoromethyl)phenoxy-17,18,19,20-tetranor-5,13-prostadienoic acid isopropyl ester (II)

Treatment of benzoate 1 [for the synthesis of 1, see Verdoorn et. al. *Synthetic Communications*, 22:1813–29 (1992)] with $K_2CO_3$ in methanol affords alcohol 2, which is oxidized using pyridinium dichromate in $CH_2Cl_2$ to afford aldehyde 3. Condensation of 3 with $(MeO)_2P(O)CH_2C(O)CH_2OC_6H_4\text{-}p\text{-}CF_3$ in the presence of $NEt_3$ and LiCl in THF provides enone 4, which is reduced with $NaBH_4$ in methanol in the presence of $CeCl_3$ to give allyl alcohol 5 after chromatographic separation of carbon-15 alcohol diastereomers. The lactone is reduced to lactol 6 using diisobutylaluminum hydride (DIBAL-H) in toluene at $-78\,°$ C. Condensation of 6 with $Ph_3P^+(CH_2)_4CO_2H\,Br^-$ in tetrahydrofuran (THF) in the presence of potassium tert-butoxide (KOBu$^t$), followed by treatment of the intermediate eneacid with isopropyl iodide and 1,8-diazabicyclo[5.4.0]undec-7-ene (DBU) in acetone yields protected ester 7, which is treated sequentially with trimethylsilyl trifluoromethanesulfonate (TMSOTf) and tetra-n-butylammonium fluoride (TBAF) in THF to afford II.

EXAMPLE 2:

Synthesis of III

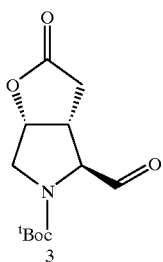

3

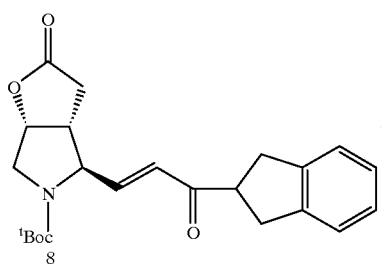

8

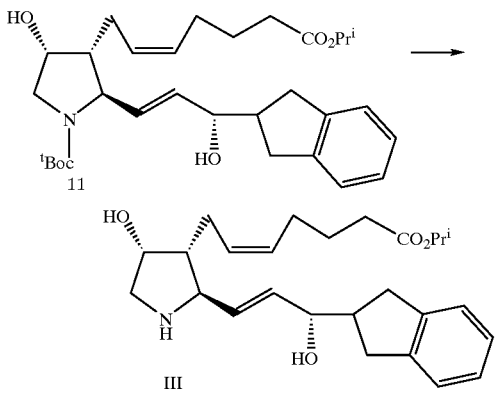

(5Z,13E)-(9R,15S)-11-Aza-9,15-dihydroxy-15-(2-indanyl)-16,17,18,19,20-pentanor-5,13-prostadienoic acid isopropyl ester (III)

Condensation of aldehyde 3 with dimethyl 2-oxo-2-(2-indanyl)ethylphosphonate in the presence of $NEt_3$ and LiCl in THF provides enone 8, which is reduced with $NaBH_4/CeCl_3$ in methanol to afford, after chromatographic separation of carbon 15 alcohol diastereomers, allyl alcohol 9. The lactone is reduced to lactol 10 using DIBAL-H in toluene at $-78\,°$ C. Condensation of 10 with $Ph_3P^+(CH_2)_4CO_2H\,Br^-$ in THF in the presence of KOBu$^t$, followed by treatment of the intermediate eneacid with isopropyl iodide and DBU in acetone yields protected ester 11, which is treated sequentially with trimethylsilyl trifluoromethanesulfonate TMSOTf and TBAF in THF to afford III.

EXAMPLE 3:

Synthesis of IV

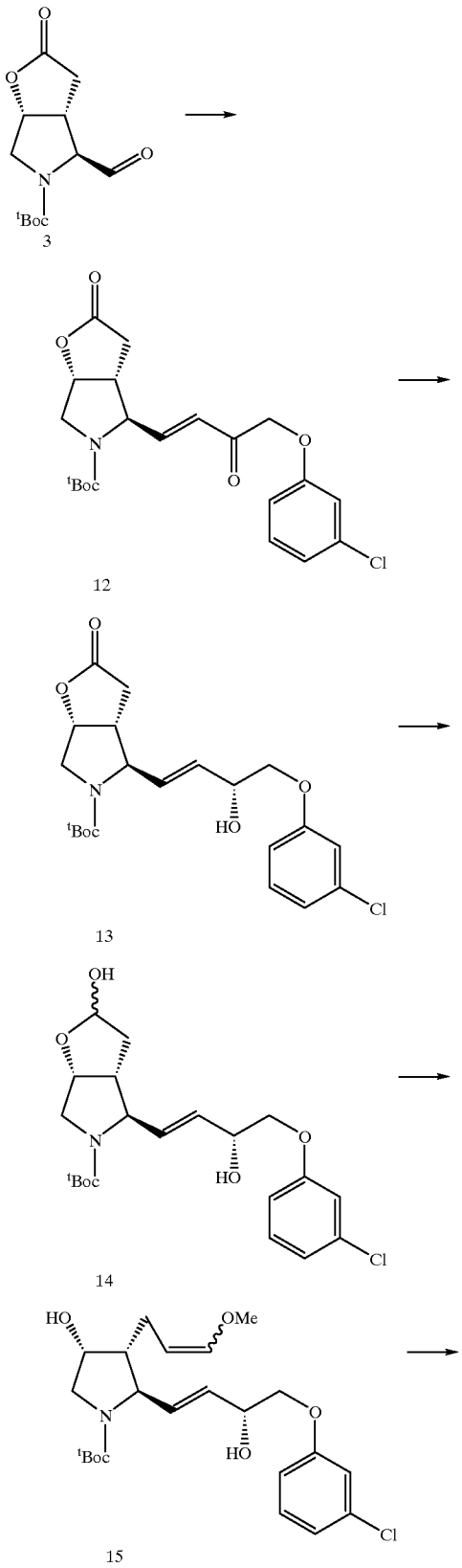
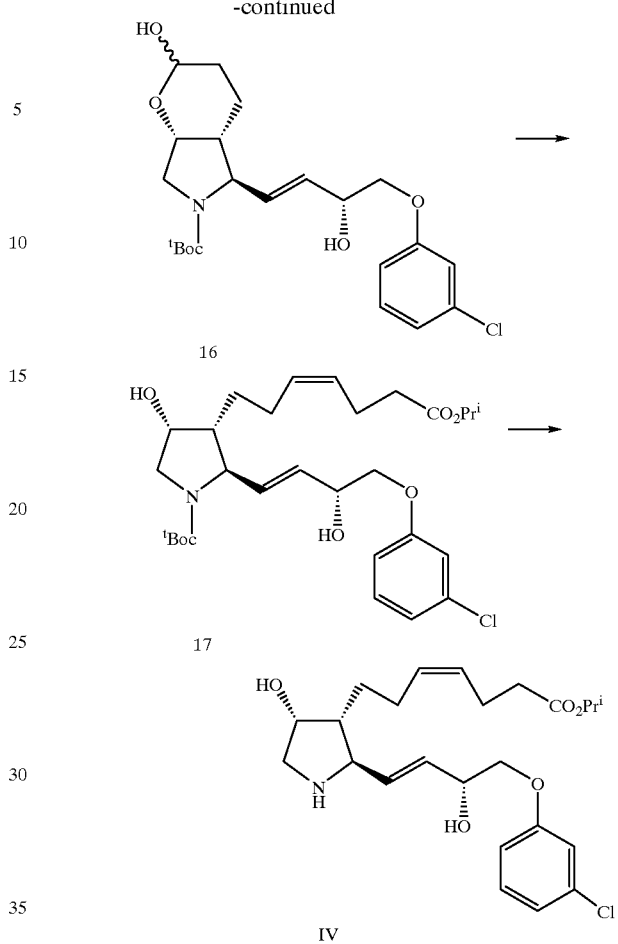

(4Z 13E)-(9R 15R)-11-Aza-16-(3-chlorophenoxy)-9, 15-dihydroxy-17,18,1 9,20-tetranor-4,13-prostadienoic acid isopropyl ester (IV)

Condensation of aldehyde 3 with $(MeO)_2P(O)CH_2C(O)CH_2OC_6H_4$-m-Cl in THF in the presence of $NEt_3$ and LiCl affords enone 12, which which is reduced with $NaBH_4/CeCl_3$ in methanol to afford, after chromatographic separation of carbon 15 alcohol diastereomers, allyl alcohol 13. The lactone is reduced to lactol 14 using DIBAL-H in toluene at $-78°$ C. Condensation of 14 with $Ph_3P^+CH_2OMe$ $Cl^-$ in THF in the presence of $KOBu^t$ yields enol ether 15, which is hydrolyzed to lactol 16 using p-toluenesulfonic acid in hot THF/water. Condensation of 16 $Ph_3p^+(CH_2)_3CO_2H\ Br^-$ in THF in the presence of $KOBu^t$, followed by treatment of the intermediate eneacid with isopropyl iodide and DBU in acetone yields protected ester 17, which is treated sequentially with trimethylsilyl trifluoromethanesulfonate TMSOTf and TBAF in THF to afford IV.

The 11-aza prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the cyclohexyl prostaglandins of the present invention include the following Examples 4–6:

EXAMPLE 4:

| Ingredient | Amount (wt %) |
|---|---|
| Compound II | 0.01 |
| Phosphate Buffered Saline | 1.0 |
| Polysorbate 80 | 0.5 |
| Purified water | q.s. to 100% |

EXAMPLE 5:

| Ingredient | Amount (wt %) |
|---|---|
| Compound III | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 6:

| Ingredient | Amount (wt %) |
|---|---|
| Compound IV | 0.1 |
| Phosphate Buffered Saline | 1.0 |
| Hydroxypropyl-β-cyclodextrin | 4.0 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of formula I:

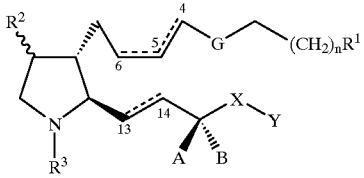

wherein:
$R^1 = CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$ = same or different = H or alkyl;
$R^6$ = H, acyl, or alkyl;
$R^7$, $R^8$ = same or different = H, acyl, or alkyl; with the proviso that if one of R$^7$, R$^8$=acyl, then the other=H or alkyl;

n=0 or 2;

G=CH$_2$ or O;

R$^2$=H, OH, acyloxy, or alkoxy;

----=single or non-cumulated double bond, with the provisos that when G=O, a single bond exists between carbons 4 and 5, and that if a double bond is present between carbons 13 and 14 that it be of the trans configuration;

R$^3$=H, R$^{11}$, COR$^{11}$, or CO$_2$R$^{11}$, where R$^{11}$=alkyl;

one of A, B=H, the other=F, OH, acyloxy, or alkoxy;

or A-B=O(CH$_2$)$_2$O or O as a carbonyl;

X=(CH$_2$)$_q$ or (CH$_2$)$_q$O; where q=1–6; and

Y=a phenyl ring optionally substituted with alkyl, halo, trihalomethyl, alkoxy, acyl acyloxy, amino, alkylamino, acylamino, or hydroxy; or X-Y=(CH$_2$)$_p$Y$^1$; where p=0–6; and

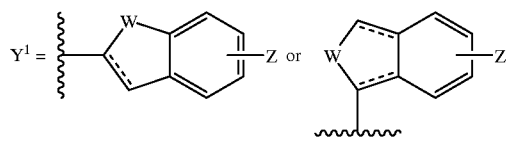

wherein:

W=CH$_2$, O, S(O)$_m$, NR$^9$, CH$_2$CH$_2$, CH=CH, CH$_2$O, CH$_2$S(O)$_m$, CH=N, or

CH$_2$NR$^9$; where m=0–2, and R$^9$=H, alkyl, or acyl;

Z=H, alkyl, alkoxy, acyl, acyloxy, halo, trihalomethyl, amino, alkylamino, acylamino, or hydroxy; and ----=single or double bond.

2. The method of claim 1, wherein the compound is administered topically.

3. The method of claim 2, wherein the compound is administered as a solution, suspension, or emulsion in an ophthalmically acceptable vehicle.

4. The method of claim 2, wherein the concentration of the compound is between about 0.00003 to about 0.5 weight percent.

5. The method of claim 4, wherein the concentration of the compound is between about 0.0005 to about 0.03 weight percent.

6. The method of claim 5, wherein the concentration of the compound is between about 0.001 to about 0.01 weight percent.

7. The method of claim 1, wherein for the compound of formula I:

R$^1$=CO$_2$R, where R=H or CO$_2$R forms an ophthalmically acceptable ester moiety;

n=0;

G=CH$_2$;

----=a single or non-cumulated double bond, with the provisos that a double bond between carbons 4 and 5 may not be of the trans configuration, and that a trans double bond exists between carbons 13 and 14;

R$^2$=OH in the alpha configuration;

R$^3$=H;

A=H, and B=OH;

X=CH$_2$CH$_2$ or CH$_2$O;

Y=phenyl optionally substituted with halo or trihalomethyl;

or, X-Y=(CH$_2$)$_p$Y$^1$, where p=0 and

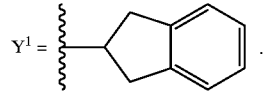

8. The method of claim 7, wherein the compound is:

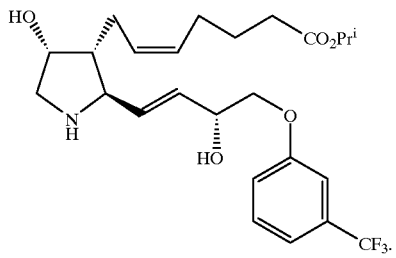

9. The method of claim 7, wherein the compound is:

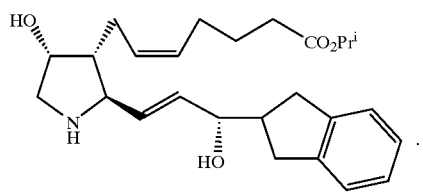

10. The method of claim 7, wherein the compound is:

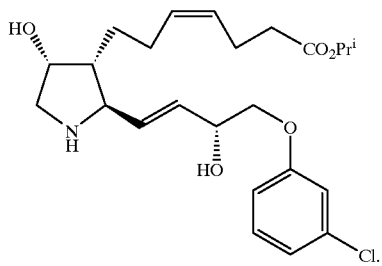

11. A compound of formula I:

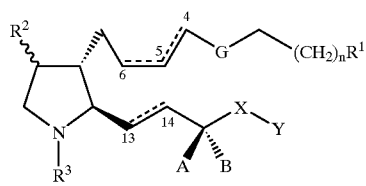

wherein:

R$^1$=CO$_2$R, CONR$^4$R$^5$, CH$_2$OR$^6$, or CH$_2$NR$^7$R$^8$; where:

R=H or cationic salt moiety, or CO$_2$R forms a pharmaceutically acceptable ester moiety;

R$^4$, R$^5$=same or different=H or alkyl;

R$^6$=H, acyl, or alkyl;

R$^7$, R$^8$=same or different=H, acyl, or alkyl; with the proviso that if one of R$^7$, R$^8$=acyl, then the other=H or alkyl;

n=0 or 2;

G=$CH_2$ or O;

$R^2$=H, OH, acyloxy, or alkoxy;

----=single or non-cumulated double bond, with the provisos that when G=O, a single bond exists between carbons 4 and 5, and that if a double bond is present between carbons 13 and 14 that it be of the trans configuration;

$R^3$=H, $R^{11}$, $COR^{11}$, or $CO_2R^{11}$, where $R^{11}$=alkyl;

one of A, B=H, the other=F, OH, acyloxy, or alkoxy;

or A-B=$O(CH_2)_2O$ or O as a carbonyl;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=$(CH_2)_pY^1$; where p=0–6; and

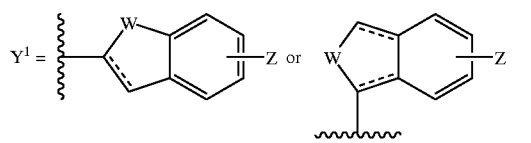

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and ----=single or double bond.

12. The compound of claim 11, wherein:

$R^1$=$CO_2R$, where R=H or $CO_2R$ forms an ophthalmically acceptable ester moiety;

n=0;

G=$CH_2$;

----=a single or non-cumulated double bond, with the provisos that a double bond between carbons 4 and 5 may not be of the trans configuration, and that a trans double bond exists between carbons 13 and 14;

$R^2$=OH in the alpha configuration;

$R^3$=H;

A=H, and B=OH;

X=$CH_2CH_2$ or $CH_2O$;

Y=phenyl optionally substituted with halo or trihalomethyl;

or, X-Y=$(CH_2)_pY^1$, where p=0 and

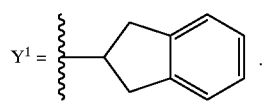

13. The compound of claim 12, having the formula:

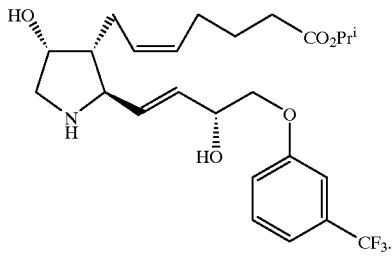

14. The compound of claim 12, having the formula:

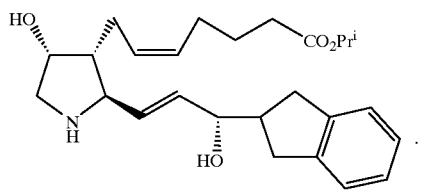

15. The compound of claim 12, having the formula:

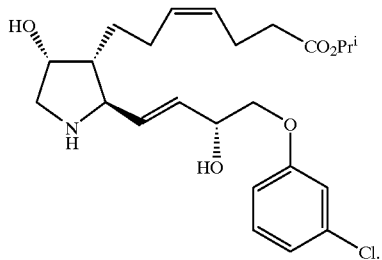

16. An ophthalmic composition for the treatment of glaucoma and ocular hypertension, comprising a compound of formula I:

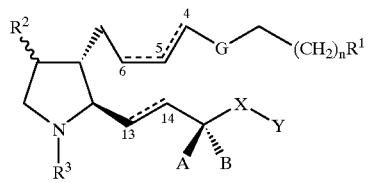

wherein:

$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;

$R^4$, $R^5$=same or different=H or alkyl;

$R^6$=H, acyl, or alkyl;

$R^7$, $R^8$=same or different=H, acyl, or alkyl; with the proviso that if one of
$R^7$, $R^8$=acyl, then the other=H or alkyl;

n=0 or 2;

G=$CH_2$ or O;

$R^2$=H, OH, acyloxy, alkoxy;

----=single or non-cumulated double bond, with the provisos that when G=O, a single bond exists between carbons 4 and 5, and that if a double bond is present between carbons 13 and 14 that it be of the trans configuration;

$R^3$=H, $R^{11}$, $COR^{11}$, or $CO_2R^{11}$, where $R^{11}$=alkyl;

one of A, B=H, the other=F, OH, acyloxy, or alkoxy;

or A-B=$O(CH_2)_2O$ or O as a carbonyl;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=$(CH_2)_pY^1$; where p=0–6; and

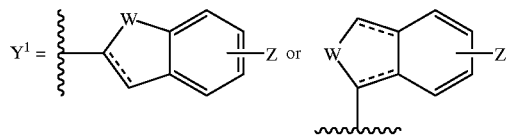

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and

- - - =single or double bond; and an ophthalmically acceptable vehicle therefor.

17. The composition of claim 16, wherein for the compound of formula I:

$R^1$=$CO_2R$, where R=H or $CO_2R$ forms an ophthalmically acceptable ester moiety;

n=0;

G=$CH_2$;

- - - =a single or non-cumulated double bond, with the provisos that a double bond between carbons 4 and 5 may not be of the trans configuration, and that a trans double bond exists between carbons 13 and 14;

$R^2$=OH in the alpha configuration;

$R^3$=H;

A=H, and B=OH;

X=$CH_2CH_2$ or $CH_2O$;

Y=phenyl optionally substituted with halo or trihalomethyl;

or, X-Y=$(CH_2)_pY^1$, where p=0 and

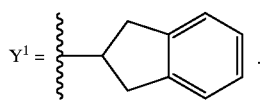

18. The composition of claim 17, wherein the compound has the formula:

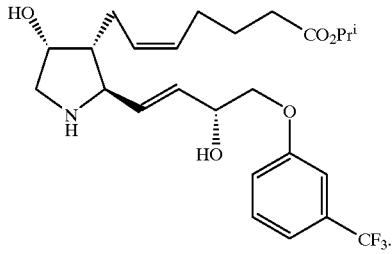

19. The composition of claim 17, wherein the compound has the formula:

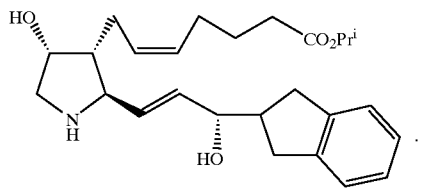

20. The composition of claim 17, wherein the compound has the formula:

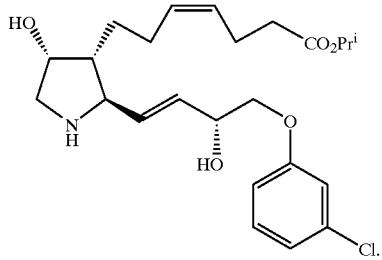

* * * * *